(12) United States Patent
Haire et al.

(10) Patent No.: US 7,053,781 B1
(45) Date of Patent: May 30, 2006

(54) APPARATUS FOR INCONTINENCE DETECTION AND NOTIFICATION

(76) Inventors: Glen Haire, 1500 W. Parrish, Owensboro, KY (US) 42301; Daniel R. Bowe, 1980 Route 75, Kenova, WV (US) 25530; Terry L. Lakin, 2655 Huntington Rd., Apple Grove, WV (US) 25502

( * ) Notice: Subject to any disclaimer, the term of this patent is extended or adjusted under 35 U.S.C. 154(b) by 2 days.

(21) Appl. No.: 10/843,818

(22) Filed: May 12, 2004

Related U.S. Application Data

(60) Provisional application No. 60/471,625, filed on May 19, 2003.

(51) Int. Cl.
*G08B 21/00* (2006.01)
(52) U.S. Cl. .................... 340/604; 340/573.5; 340/605
(58) Field of Classification Search ............ 340/573.5, 340/604, 605, 652
See application file for complete search history.

(56) References Cited

U.S. PATENT DOCUMENTS

| | | | |
|---|---|---|---|
| 4,977,906 A * | 12/1990 | Di Scipio | 128/885 |
| 5,153,564 A * | 10/1992 | Hoiberg | 340/604 |
| 5,463,377 A * | 10/1995 | Kronberg | 340/605 |
| 5,557,263 A * | 9/1996 | Fisher et al. | 340/605 |
| 5,760,694 A * | 6/1998 | Nissim et al. | 340/604 |
| 5,808,554 A * | 9/1998 | Shuminov | 340/604 |
| 6,373,395 B1 * | 4/2002 | Kimsey | 340/602 |
| 6,753,783 B1 | 6/2004 | Friedman et al. | |

OTHER PUBLICATIONS

PPP Enterprises, Inc., www.WeBehave.com, Stay-Dri Deep Sleep Alarm marketing material downloaded at www. webehave.com/wetalarm.htm on Mar. 25, 2003, 2 pages.
Disability Supplies.Com online Catalogue downloaded at http://www.disabilitysupplies.co.uk/acatalog/Online_Catalogue_General_25.html. on Mar. 25, 2003, 1 page.
Colonial Medical, Vibrawake Multi-Tone Drinite Personal Enuresis Alarm marketing material downloaded at http://colonialmedical.com/76323.htm on Mar. 25, 2003, 1 page.
Enuresis Alarm marketing material downloaded at http://www.enablingdevices.com/store/iteminfo.cfm?ID=220 on Mar. 25, 2003, 1 page.

(Continued)

*Primary Examiner*—Benjamin C. Lee
*Assistant Examiner*—Travis Hunnings
(74) *Attorney, Agent, or Firm*—Stites & Harbison, PLLC; David W. Nagle, Jr.; Mandy W. Decker

(57) ABSTRACT

An apparatus for incontinence detection and notification comprises a notification component, for providing notice that an incontinent event has occurred, and a sensor. The sensor includes a sensing pad for collecting and retaining fluid resulting from the incontinent event, and a circuit housed within the sensing pad. The circuit has a pair of stainless steel electrodes, which are in electronic communication with the notification component. A closed circuit is created between the electrodes by the fluid resulting from the incontinent event, causing an electronic signal to be communicated to the notification component. The circuit may also include a plurality of connectors placed in electronic communication with the notification component to diagnose a disconnected or poorly connected circuit.

13 Claims, 2 Drawing Sheets

OTHER PUBLICATIONS

Malem, Enuresis & Bedwetting Resources Pack marketing material, downloaded at http://www.enursis.com.au/ on Mar. 19, 2003, 1 page.

Malem, Remote Wetness Alarm marketing material downloaded at http://www.enuresis.com.au/otherpro/info.html on Mar. 19, 2003, 2 pages.

Malem, Enuresis Products Pricelist, downloaded at http:www/enuresis.com.au/order/pricelist_prohtml on Mar. 19, 2003, 2 pages.

Malem Medical, enuresis alarm marketing material downloaded at http://www.malem.co.uk/audio.htm on Mar. 25, 2003, 1 page.

Malem Medical, enuresis alarm marketing material downloaded at http://www.malem.co.uk/wireless.htm, 1 page.

Malem Medical, Easy-clip sensor marketing material downloaded at http://www.malem.co.uk/sensors.htm on Mar. 25, 2003, 2 page.

Neen Healthcare, The Permanent Cure for Bedwetting, marketing material downloaded at http:/www/neenhealth.com/continence/malem/default.htm on Mar. 25, 2003, 2 pages.

Easylink UK, Bed Wetting Enuresis Alarm marketing material, downloaded at http://easylinkuk.co.uk/page11.html on Mar. 25, 2003, 4 pages.

Quirosa,S.A., Enuresis Alarms marketing material, downloaded at http://www/quirosa.com/quiros/230002i.htm on Mar. 25, 2003, 3 pages.

Alpha Consultants, DRI Sleeper marketing material, downloaded at http://www.dri-sleeper.com/product.htm on Mar. 25, 2003, 4 pages.

Enura AB, Enurad 400 marketing material, downloaded at http://enurad.com/ on Mar. 25, 2003, 3 pages.

Travis International, Inc., product marketing material, downloaded at http://www.travisinternational.com/cgi-local/SoftCart.10.exe/online-store/scstore/p-. . . on Mar. 25, 2003, 8 pages.

Allegromedical.com, bedwetting products marketing material, downloaded at http://www.allegromedical.com/home/moreinfo.asp?C=525&S=3660&M=15298&P=1774 . . . on Mar. 25, 2003, 2 pages.

NAFC, Alarms/Signaling Devices and Monitoring Systems product information, downloaded at http://www.nafc.org/site/members/private/resource . . . on Mar. 25, 2003, 4 pages.

Enuresis Moisture Alarms, product information, downloaded at http://www.wetbuster.com/alarms.htm on Mar. 25, 2003, 2 pages.

Twin Rivers, Inc., Kno-Wet-All marketing brochure, Oct. 2000, 4 pages, Livermore, Kentucky.

* cited by examiner

APPARATUS FOR INCONTINENCE DETECTION AND NOTIFICATION

CROSS REFERENCES TO RELATED APPLICATIONS

This application claims priority to U.S. Provisional Application Ser. No. 60/471,625 filed May 19, 2003, the entire disclosure of which is incorporated herein by this reference.

FIELD OF THE INVENTION

The present invention relates to the detection of electrically conductive fluids, such as bodily fluids from human beings, including urine and feces.

BACKGROUND OF THE INVENTION

In nursing homes and similar care facilities, resident incontinence is a prevalent problem. Failure to promptly respond to and assist incontinent residents after the occurrence of an incontinent event can result in infections, pressure ulcers, and other medical complications. Therefore, the nursing home and healthcare industry has sought to develop an effective apparatus for detecting the occurrence of incontinent events.

In this regard, apparatus have been pursued that include one or more sensors comprising a pair of electrodes connected with a voltage source, an audible alarm being activated when an electrically conductive fluid completes the circuit between the electrodes. However, such prior art apparatus are rife with problems. For example, many prior art sensors are not suitable for reuse because the sensors cannot withstand the heat and chemical treatments necessary for cleaning or sterilization. For another example, prior art apparatus do not allow for the detection of a disconnected or poorly connected circuit associated with the sensor.

Accordingly, there remains a need in the art for an apparatus for incontinence detection and notification that overcomes these problems.

SUMMARY OF THE INVENTION

The present invention meets the above identified needs, and others, by providing an apparatus for incontinence detection and notification that can withstand rigorous heat and chemical cleaning such that the apparatus is reusable. The apparatus of the present invention also includes a sensor component that allows for the detection of a disconnected or poorly connected circuit. The apparatus of the present invention further provides for notification of an incontinent event through transmission of a signal to a remote receiver or monitoring station, along with the collection, storage, and analysis of data related to incontinent events.

An exemplary embodiment of the apparatus of the present invention includes a sensor for detecting the occurrence of an incontinent event and a notification component. The sensor generally comprises a washable multi-layered sensing pad with a detection circuit integrated therein, the detection circuit having a positive electrode and a negative electrode. The sensing pad is designed to be placed into contact with or worn by an individual. The electrodes may be constructed from a material, such as stainless steel, that is not only a conductor, but has the ability to withstand harsh heat and chemical treatments. As such, the entire sensor, including the sensing pad and the detection circuit, may be cleaned or sanitized and thereafter reused. When an incontinent event occurs, the resulting fluid is absorbed by the soaking pad, thereby creating a closed circuit between the positive electrode and the negative electrode and communicating to the notification component that an incontinent event has occurred.

In addition to the electrodes, the detection circuit may include a pair of connectors associated with the positive electrode and a pair of connectors associated with the negative electrode. The connectors connect the detection circuit to the notification component. The connectors additionally allow for the detection of a disconnected or poorly connected circuit. In this regard, each pair of connectors is placed in electronic communication with one another using a jumper and a closed jumper circuit is formed therebetween. Accordingly, when the circuit becomes disconnected or poorly connected, one or both of the jumper circuits becomes opened. All four connectors are placed in electronic communication with the notification component; as such, the change between an opened and closed configuration of either jumper circuit causes an electronic signal to be communicated to the notification component.

DESCRIPTION OF THE INVENTION

Figure 1:
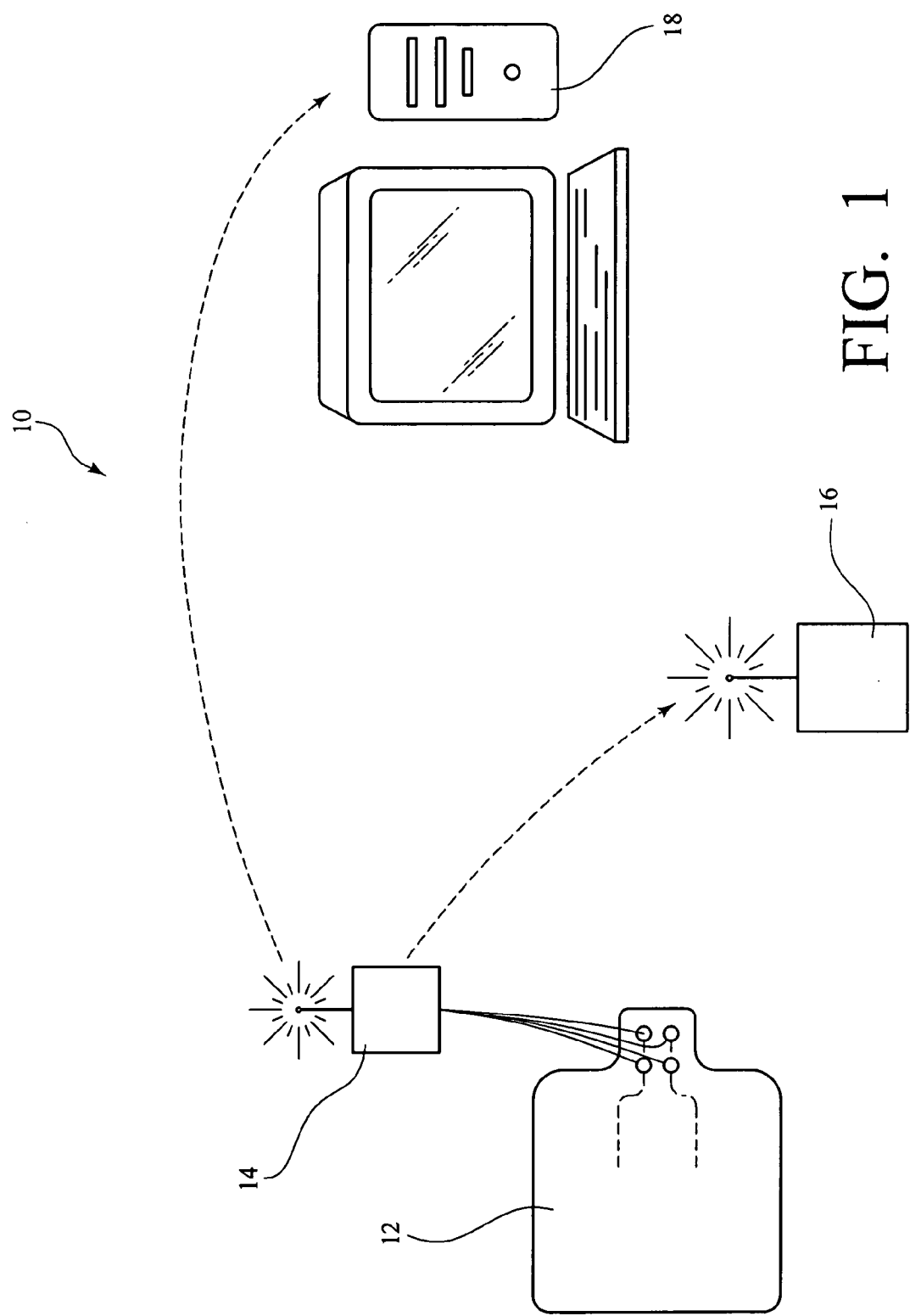
FIG. 1 is an schematic view of an exemplary embodiment of an apparatus made in accordance with the present invention.

The present invention is an apparatus for incontinence detection and notification. With reference to FIG. 1, an exemplary embodiment of the apparatus 10 generally includes a sensor 12 for detecting the occurrence of an incontinent event, and a notification component 14, which is depicted as a wireless transmitter in FIG. 1. Furthermore, in this exemplary embodiment, the apparatus 10 includes a remote receiver or monitoring station 16 (e.g., pager or other wireless receiver) for receiving a notification of and/or data regarding the incontinent event from the notification component 14. Lastly, in this exemplary embodiment, the apparatus 10 includes an analysis component 18, such as computer and associated software, for collecting, storing, and analyzing data related to incontinent events.

Figure 2:
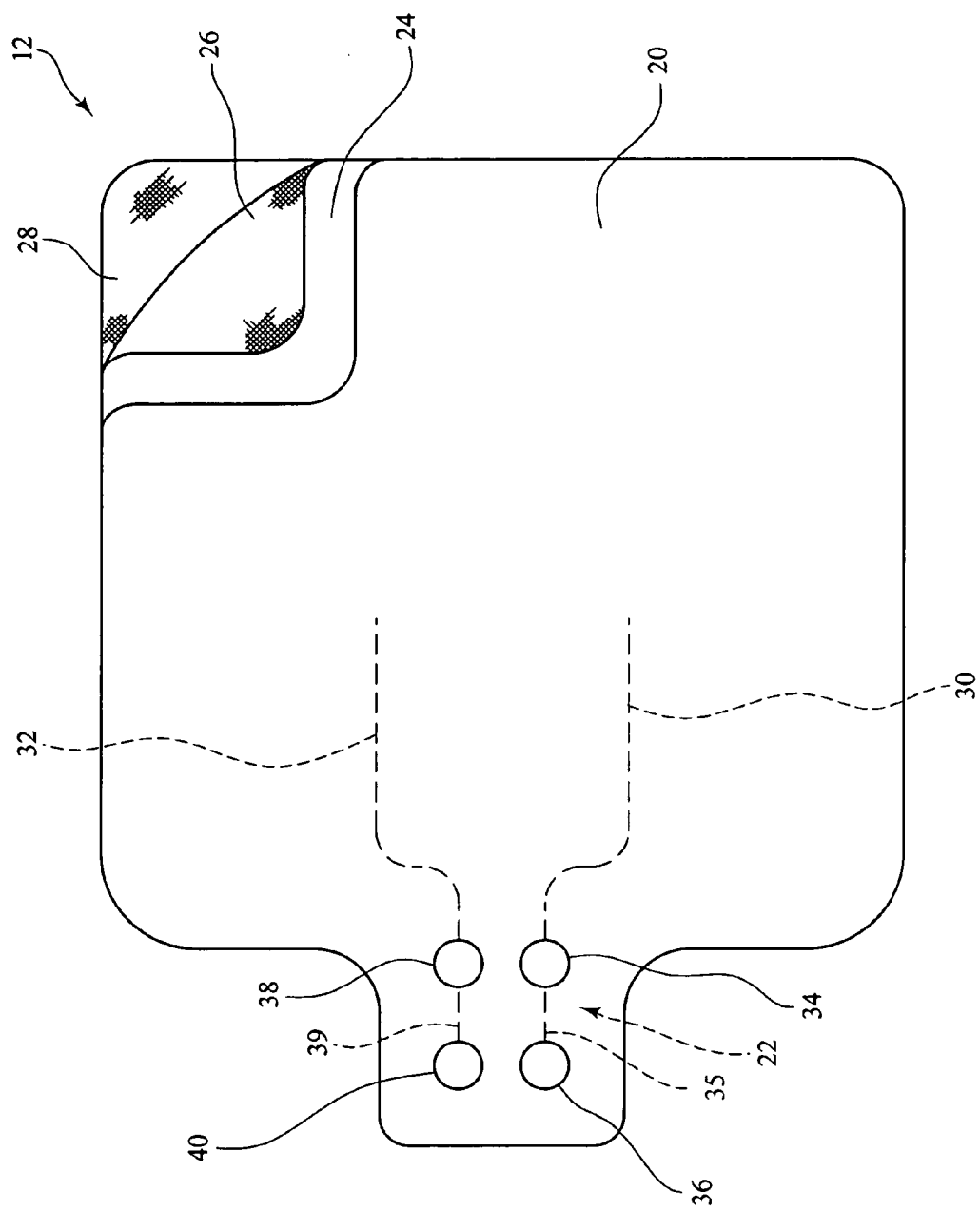
FIG. 2 is a plan view of the sensor of the exemplary embodiment depicted in FIG. 1.

Turning now to FIG. 2, the sensor 12 in this exemplary embodiment includes a washable multi-layered sensing pad 20 with a detection circuit 22 integrated therein, the detection circuit 22 having a pair of electrodes, one being positive 30 and the other being negative 32. The sensing pad 20 is designed to be placed into contact with or worn by an individual, much like a diaper or similar undergarment. In this exemplary embodiment, the sensing pad 20 is comprised of three distinct layers of material bonded together and housing the detection circuit 22. Specifically, the sensing pad 20 includes a first layer 24 of a washable material, such as polyester tricot, that contacts the wearer's skin. This first layer 24 is quilted or similarly joined to a second layer 26 of washable soaker material, which absorbs moisture in a manner similar to a diaper. The pair of electrodes 30, 32 are secured to this second layer 26. Finally, a third layer 28 of fluid-resistant material, such as vinyl, may be joined to the first two layers 24, 26, thereby enclosing the electrodes 22 within the sensing pad 20. This third layer 28 prevents moisture from escaping from the sensing pad 20.

The electrodes 30, 32 of the detection circuit 22 are constructed from a material, such as stainless steel, that is not only a conductor, but has the ability to withstand harsh heat and chemical treatments. For example, the electrodes 30, 32 may be constructed from Bekinox-VN12/4X275/100S stainless steel continuous filament yarn, which is manufactured and distributed by Bekaert Fiber Technologies of Research Triangle Park, N.C. As such, the entire sensor 12 may be cleaned or sanitized and thereafter reused. Alternatively, if the sensor 12 is to be disposable, and thus not subject to cleaning and sanitization, a less expensive metal conductor may be used.

An open circuit is maintained between the positive electrode 30 and the negative electrode 32. When an incontinent event occurs, the resulting fluid is absorbed by the second layer 26 soaker material, thereby creating a closed circuit between the positive electrode 30 and the negative electrode 32. Since the electrodes 30, 32 are placed in electric communication with the notification component 14, the closing of the circuit is immediately communicated to the notification component 14, as is further described below. Furthermore, it should be recognized that the electrodes 30, 32 are secured to the sensing pad 20 in a predetermined configuration because the distance between the electrodes 30, 32 determines the amount of fluid that has to be absorbed by the second layer 26 of soaker material before the circuit is completed. In other words, there is a correlation between the configuration of the electrodes 30, 32 and the sensitivity of the sensor 12. Of course, although the electrodes 30, 32 are illustrated as being configured in two substantially parallel lines in this exemplary embodiment, various other configurations could be employed without departing from the spirit and scope of the present invention.

Although it is not necessary for the operation of the circuit in detecting incontinent events, in the depicted embodiment of the apparatus 10, in addition to the electrodes 30, 32, the detection circuit 22 includes a plurality of connectors 34, 36, 38, 40, which allow for the physical and electrical connection of the circuit 22 to the notification component 14. The connectors 34, 36, 38, 40 additionally allow for the detection of a disconnected or poorly connected circuit, as will be described further below. In this exemplary embodiment, the connectors 34, 36, 38, 40 are constructed from a material, such as stainless steel, and may be SW-30 series snaps manufactured by YKK Universal Fasteners, Inc. of Lawrenceburg, Ky.

Specifically, with reference to FIG. 2, the circuit 22 includes a first and a second connector 34, 36 associated with the positive electrode 30 and a third and a fourth connector 38, 40 associated with the negative electrode 32. The distal end of the positive electrode 30 is placed in electronic communication with the first connector 34, while the distal end of the negative electrode 32 is placed in electronic communication with the third connector 38. The first connector 34 is additionally placed in electronic communication with the second connector 36 using a jumper 35, while the third connector 38 is additionally placed in electronic communication with the fourth connector 40 using a jumper 39. As such, a closed jumper circuit is created between the first and second connectors 34, 36, and a similar jumper circuit is created between the third and fourth connectors 38, 40. Like the electrodes, the jumpers 35, 39 are constructed from a material that is not only a conductor, but also has the ability to withstand harsh heat and chemical treatments, for example, Bekinox-VN12/4X275/100S stainless steel continuous filament yarn, which is manufactured and distributed by Bekaert Fiber Technologies of Research Triangle Park, N.C.

Accordingly, the notification component 14 not only monitors the open circuit between the electrodes 30, 32, but also monitors the closed jumper circuits. When an electrically conductive fluid absorbed into the second layer 26 of soaker material has closed the circuit between the electrodes 30, 32, that change is communicated to the notification component 14. Likewise, when the detection circuit 22 becomes disconnected or poorly connected, the jumper circuit between either the first and second connectors 34, 36 or the third and fourth connectors 38, 40 becomes opened. This change in either jumper circuit also causes an electronic signal to be communicated to the notification component 14. For example, if any of the four connectors 34, 36, 38, 40 become disconnected, perhaps during cleaning and sanitization, there will be an open circuit condition communicated to the notification component 14, indicating that the sensor 12 can not function.

In the depicted embodiment, the notification component 14 is a wireless transmitter; however, it could be a visible or audible alarm or similar device without departing from the spirit and scope of the present invention. In any event, it is contemplated that the notification component 14 is designed to be waterproof and includes a battery or similar power source for powering the detection circuit 22. Once an electrically conductive fluid absorbed into the second layer 26 of soaker material has closed the circuit, the wireless transmitter 14 is activated to notify a remote receiver or monitoring station 16. This allows a caregiver to immediately respond and provide appropriate care for the incontinent individual. Furthermore, signals from multiple sensors may be received and identified by the remote monitoring station 16, thereby allowing for more effective scheduling of rounds by the caregivers.

Finally as mentioned above, the notification component 14 (e.g., wireless transmitter) may be capable of transmitting information to an analysis component 18, such as computer and associated software, for collecting, storing, and analyzing data related to incontinent events.

It will be obvious to those skilled in the art that further modifications may be made to the embodiments described herein without departing from the spirit and scope of the present invention.

What is claimed is:

1. An apparatus for incontinence detection and notification, comprising:
 a notification component for providing notice that an incontinent event has occurred; and
 a washable sensor, including
  a sensing pad for collecting and retaining fluid resulting from the incontinent event, said sensing pad including a first layer of a washable material for contacting the skin of a wearer, a second layer of washable soaker material for absorbing the fluid resulting from the incontinent event, and a third layer of fluid-resistant material joined to said first and second layers, said third layer preventing fluid from escaping from the sensing pad, and
  a circuit integrated within the second layer of said sensing pad having a first and a second electrode, a closed circuit being created between said electrodes by the fluid resulting from the incontinent event, causing an electronic signal to be communicated to the notification component;

wherein said electrodes are constructed from a material having the ability to withstand harsh heat and chemical treatments, such that said sensor, including the sensing pad and integrated circuit, may be cleaned, sanitized, and thereafter reused.

2. The apparatus as recited in claim 1, wherein the notification component is a transmitter.

3. The apparatus as recited in claim 2, and further comprising a remote receiver for receiving a notification of and/or data regarding the incontinent event from the notification component.

4. The apparatus as recited in claim 3, and further comprising an analysis component receiving information from the notification component for collecting, storing, and analyzing data related to incontinent events.

5. The apparatus as recited in claim 2, and further comprising an analysis component receiving information from the notification component for collecting, storing, and analyzing data related to incontinent events.

6. The apparatus as recited in claim 1, wherein said electrodes are constructed from stainless steel.

7. The apparatus as recited in claim 6, wherein said electrodes are constructed from a stainless steel continuous filament yarn.

8. An apparatus for incontinence detection and notification, comprising:
   a notification component for providing notice that an incontinent event has occurred; and
   a sensor, including
      a sensing pad for collecting and retaining fluid resulting from the incontinent event, and
      a circuit housed within the sensing pad having a first and a second electrode, a closed circuit being created between said electrodes by the fluid resulting from the incontinent event, causing an electronic signal to be communicated to the notification component, the circuit further including
         a first connector placed in electronic communication with the first electrode;
         a second connector placed in electronic communication with the first connector;
         a third connector placed in electronic communication with the second electrode; and
         a fourth connector placed in electronic communication with the third connector,
      wherein a closed circuit is created between the first and second connectors and another closed circuit is created between the third and fourth connectors, and all connectors are placed in electronic communication with the notification component, an electronic signal being communicated to the notification component upon the formation of an open circuit between the connectors, indicating that the sensor can not function.

9. The apparatus as recited in claim 8, wherein the notification component is a transmitter.

10. The apparatus as recited in claim 9, and further comprising a remote receiver for receiving a notification of and/or data regarding the incontinent event from the notification component.

11. The apparatus as recited in claim 10, and further comprising an analysis component receiving information from the notification component for collecting, storing, and analyzing data related to incontinent events.

12. The apparatus as recited in claim 9, and further comprising an analysis component receiving information from the notification component for collecting, storing, and analyzing data related to incontinent events.

13. The apparatus as recited in claim 8, wherein the electrodes are constructed from stainless steel.

* * * * *